United States Patent [19]

Garwin

[11] Patent Number: 4,464,171
[45] Date of Patent: Aug. 7, 1984

[54] INTRAVASCULAR INSERTION APPARATUS AND METHOD

[76] Inventor: Mark J. Garwin, P.O. Box 4733, Odessa, Tex. 79760

[21] Appl. No.: 363,085

[22] Filed: Mar. 29, 1982

[51] Int. Cl.³ .................. A61M 5/00; A61M 25/00
[52] U.S. Cl. .................... 604/53; 604/164; 604/17.0; 128/658
[58] Field of Search .......... 604/164, 165, 168.53, 604/187, 170, 280.53; 128/658

[56] References Cited

U.S. PATENT DOCUMENTS

| | | |
|---|---|---|
| 2,256,656 | 9/1941 | Swabacker . |
| 2,346,334 | 4/1944 | Shaw . |
| 2,389,355 | 11/1945 | Goland et al. . |
| 2,770,236 | 11/1956 | Utley et al. . |
| 2,828,744 | 4/1958 | Hirsch et al. . |
| 3,094,122 | 6/1963 | Gauthier et al. . |
| 3,452,740 | 7/1969 | Muller . |
| 3,506,007 | 4/1970 | Henkin . |
| 3,515,137 | 6/1970 | Santomieri . |
| 3,547,103 | 12/1970 | Cook . |
| 3,570,485 | 3/1971 | Reilly . |
| 3,592,192 | 7/1971 | Harautuneian ............ 604/165 |
| 3,595,230 | 7/1971 | Suyeoka et al. . |
| 3,630,198 | 12/1971 | Henkin . |
| 3,633,579 | 1/1972 | Alley et al. .............. 604/164 X |
| 3,682,173 | 8/1972 | Center . |
| 3,703,174 | 11/1972 | Smith . |
| 3,727,613 | 4/1973 | Sorenson et al. . |
| 3,757,768 | 9/1973 | Kline . |
| 3,903,888 | 9/1975 | Fuchs ...................... 604/165 X |
| 3,920,013 | 11/1975 | Bodzin . |
| 3,921,631 | 11/1975 | Thompson . |
| 3,941,119 | 3/1976 | Corrales . |
| 4,033,331 | 7/1977 | Guss et al. . |
| 4,046,144 | 9/1977 | McFarlane . |
| 4,052,989 | 10/1977 | Kline . |
| 4,068,659 | 1/1978 | Moorehead . |
| 4,068,660 | 1/1978 | Beck . |
| 4,108,175 | 8/1978 | Orton ...................... 604/168 |
| 4,160,450 | 7/1979 | Doherty . |
| 4,192,305 | 3/1980 | Seberg . |
| 4,239,042 | 12/1980 | Asai . |
| 4,243,034 | 1/1981 | Brandt . |
| 4,250,881 | 2/1981 | Smith . |
| 4,274,408 | 6/1981 | Nimrod .................... 604/168 |
| 4,349,023 | 9/1982 | Gross ...................... 604/164 |
| 4,417,886 | 11/1983 | Frankhouser et al. . |

Primary Examiner—Stephen C. Pellegrino
Attorney, Agent, or Firm—E. Harrison Gilbert, III

[57] ABSTRACT

A syringe has a guide member internally associated therewith which can be advanced and retracted by actuation of the thumb of the hand which holds the syringe. A catheter is mounted on the needle of the syringe so that once the needle has been inserted into a body vessel and the lumen of the vessel has been located by manipulation of the guide member, the catheter can be moved off the needle and along the guide member into the lumen of the vessel. The apparatus is constructed and operated so that the guide member is maintained within the syringe prior to its use as a probe within the vessel. The apparatus is also constructed and operated so that the hands of the user of the apparatus need not be moved from their initial positions during the entering of the vessel and the probing for the lumen of the vessel. Additionally, the apparatus is constructed so that a suction can be applied to the fluid within the vessel to withdraw the fluid from the vessel to note when the vessel has been entered.

13 Claims, 4 Drawing Figures

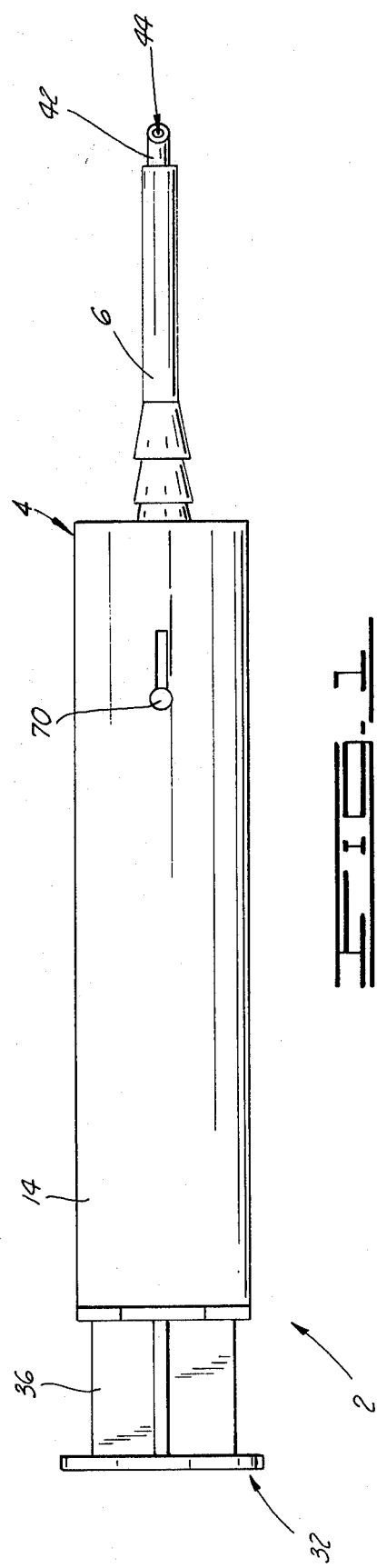
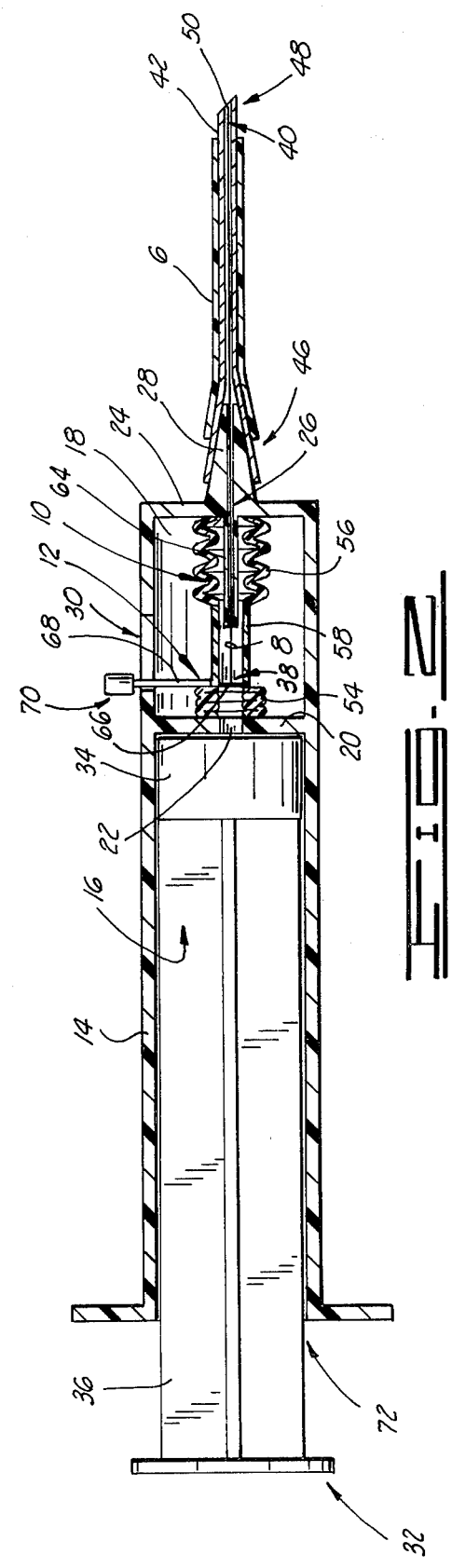

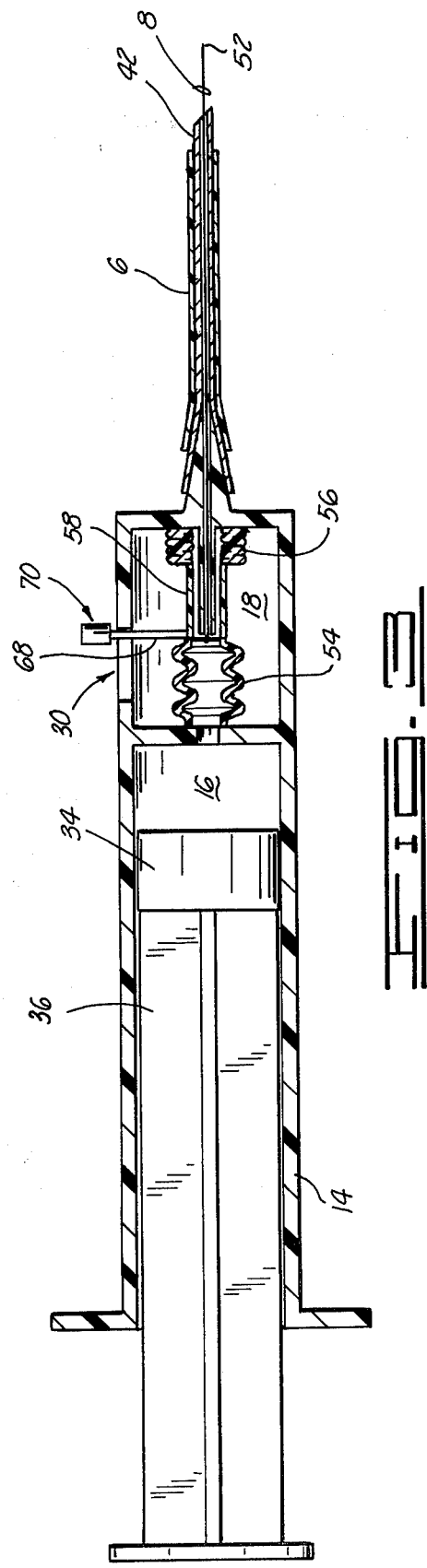
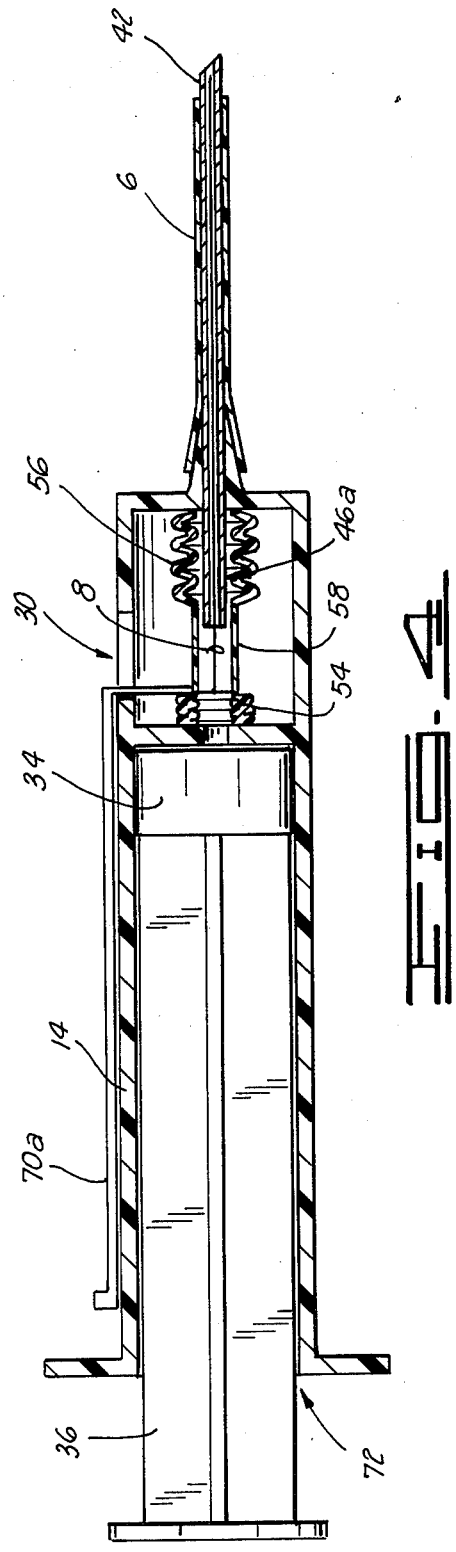

INTRAVASCULAR INSERTION APPARATUS AND METHOD

BACKGROUND OF THE INVENTION

This invention relates generally to intravascular insertion apparatus and methods and more particularly, but not by way of limitation, to an apparatus and a method for facilitating the insertion of intravascular catheters.

In anesthesiology and other medical areas it is often necessary to insert catheters into vessels within a body for either introducing substances into or extracting substances from such vessels. To properly insert a catheter into a vessel, the skin and subcutaneous tissue overlying and surrounding the vessel and the wall of the vessel itself must be pierced. Once these have been pierced, the catheter is placed within the lumen, or inner open space, of the vessel.

Although this insertion procedure seems simple, in practice it is difficult to pierce the skin, the subcutaneous tissue, and the vessel wall and ensure that the piercing ceases in the lumen so that the catheter can be properly moved into the lumen. For example, it is easy to pierce not only the near wall of the vessel but also the far wall, thereby preventing proper positioning of the catheter. Also, it is easy to only slightly pierce the near wall of the vessel so that the insertion of the catheter is made difficult. Therefore, there is the need for a device and a method for facilitating the insertion of intravascular catheters in such a manner that the chances of improperly piercing the vessel are reduced if not totally eliminated.

A current technique employed in the insertion of intravascular catheters utilizes a Teflon catheter which is seated on a steel needle forming a part of a syringe. The party who is to perform the catheter insertion grasps the patient's arm with his or her non-dominant hand (i.e., the hand not holding the catheter insertion device) and fixes the skin overlying the subcutaneous tissue and the vessel with his or her non-dominant thumb. By fixing the skin overlying the subcutaneous tissue and vessel, the relationship between these structures remains constant.

Having properly prepared the patient's arm, the party who is to insert the catheter holds the syringe-catheter assembly in his or her dominant hand (i.e., the hand other than the non-dominant hand). The dominant hand moves the syringe-catheter assembly into engagement with the patient's arm so that the needle pierces the skin and tissue overlying the vessel and enters the vessel. Applying constant suction with the syringe, the vessel is located with the return of blood into the syringe.

Upon noting that the vessel has been located, the catheter inserter attempts to pass the catheter into the vessel. At this point, however, the tip of the needle may have pierced both the near wall and the far wall of the vessel or, on the other hand, it may have only barely pierced the near wall of the vessel and thus may not be centered in the vessel. If the needle is in either of these non-centered positions, the attempt to pass the catheter into the vessel will be unsuccessful and the procedure will need to be performed again at a different site.

Besides this shortcoming of the current technique whereby the needle may not be properly centered, this procedure also has the shortcoming of requiring either the dominant hand or the nondominant hand to be moved to the catheter to push the catheter off the needle and into the vessel. This movement of either the dominant hand or the non-dominant hand prior to a definite mechanical link (such as by a guide element) being made with the lumen of the vessel increases the risk of movement of the needle relative to the vessel and the subsequent failure to maintain the catheter properly positioned within the vessel.

To assist in properly locating the lumen of the vessel and establishing a mechanical link therewith for guiding the catheter into the lumen, another current technique has utilized a separate guide wire which is to be moved into the vessel after the vessel has been located and the syringe body has been removed from the syringe needle. Once the syringe body has been removed, the guide wire which is separate from the syringe and catheter assembly is then passed through the needle and into the vessel whereupon the catheter can be passed over the guide wire and into proper position within the vessel.

This latter technique also has shortcomings. For example, the guide wire must be handled in a sterile manner to prevent the introduction of infection into the vessel; however, this is difficult because the guide wire is a separate unit and must be directly handled by the catheter inserter. To ensure the sterility of the guide wire, therefore, the inserter must sterilize the area where the catheter is to be inserted and the inserter must also wear sterile gloves. Both of these preparations are so time consuming and costly that they are usually not made until a troublesome insertion is encountered at which time it is usually too late to rectify the problem.

Another shortcoming of this latter technique is that the separation of the syringe body from the syringe needle and the insertion of the guide wire into the syringe needle requires that one or both hands be removed from their original positions. This increases the probability of movement of the needle with respect to the vessel prior to the time the guide wire can be inserted into the syringe needle.

In view of the foregoing shortcomings, there is the need for an improved intravascular insertion apparatus and method for readily locating the lumen of a vessel and for properly guiding a catheter into the lumen once it is located. This need requires the utilization of a sterile guide mechanism constructed to obviate the necessity of directly handling the guide mechanism during its use and further constructed to be moved by the same hand which holds the insertion device to obviate the necessity of removing one or both of the hands from their original positions prior to the time an adequate mechanical link can be made with the vessel.

So that the insertion device can indicate when a vessel has been located by displaying a quantity of blood flowing from the vessel, the insertion device also needs a chamber for receiving vascular fluid, such as blood, to detect when the insertion device is in the vessel. This chamber must be open to the flow of fluid from the vessel, but it also must be maintained sterile to prevent infection.

Because catheters often need to be inserted into vessels having low pressure, it is also necessary for the insertion device to include means for applying a suction to the fluid-receiving chamber to assist the extraction of a fluid from a vessel when the fluid pressure within the vessel is relatively low.

SUMMARY OF THE INVENTION

The present invention overcomes the above-noted and other shortcomings of the prior art and meets the aforementioned needs by providing a novel and improved intravascular insertion device and method. The present invention is used to readily locate the lumen of a vessel and to properly guide a catheter into the lumen. The present invention includes a sterile guide mechanism which is integrally and internally formed with the invention to preclude direct handling of the guide mechanism thereby ensuring the sterility of the guide mechanism prior to its entry into the vessel. The guide mechanism is also constructed so that it can be moved into the vessel by the same hand which holds the insertion device without requiring that hand to move from its original position.

The present invention also includes a chamber for receiving a fluid from the vessel to detect when the invention is located in the vessel prior to searching for the lumen with the guide mechanism. This chamber is open to the flow of fluid from the vessel, but is maintained in a sterile fluid pathway. The chamber can also have suction applied to it through suitable means to assist the extraction of the vascular fluid when the vascular fluid pressure is low.

Broadly, the inventive intravascular insertion apparatus includes a support body having a needle associated therewith. The needle has a passageway defined therethrough for receiving an elongated guide member slidably disposed therein. The guide member includes a first end disposed within the support body externally of the passageway of the needle. The guide member also includes a second end disposed for being movable from a first locus within the needle passageway to a second locus externally of the passageway and the support body. The insertion apparatus also includes movement means for moving the guide member between the first and second loci. A catheter having an axial opening through which the needle is slidably disposed is also included within the present invention. To receive a fluid from the passageway of the needle, the apparatus also includes side wall means associated with the support body to define a fluid-receiving chamber having an opening communicating with the passageway of the needle.

The support body includes means for limiting the length of travel of the guide member through the passageway of the needle from the first locus to the second locus. In the preferred embodiment the limiting means defines the length of travel so that the first locus is within the passageway whereby the guide member can be fully housed within the support body and needle when not in use, thereby reducing the chances of the guide member being contaminated prior to its use.

More particularly, the support body is defined as a part of a syringe. The syringe is constructed to provide suction to the fluid-receiving chamber to assist the extraction of the fluid from the vessel into which the needle is inserted.

The movement means is appropriately disposed relative to the syringe and the guide member so that the movement means can be actuated by the thumb of the dominant hand of the person inserting the catheter with the present invention. This enables the person to maintain his or her hands in their original positions until after a proper mechanical link with the vessel has been established thereby reducing the chances of losing the original relationship among the body parts and between the body parts and the present invention.

Therefore, from the foregoing, it is a general object of the present invention to provide a novel and improved intravascular insertion device and method. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a view of a first preferred embodiment of the apparatus of the present invention as viewed from above an elongated opening formed therein.

FIG. 2 is a sectional side view of the first preferred embodiment of the present invention showing the guide member in its fully retracted position.

FIG. 3 is a sectional side view of the first preferred embodiment showing the guide member in its fully extended position.

FIG. 4 is a side sectional view showing a second preferred embodiment of the present invention.

DETAILED DESCRIPTION OF THE PREFERRED EMBODIMENTS

With reference to the drawings the preferred embodiments of the present invention will be described. FIG. 1 shows that the invention includes an intravascular insertion apparatus 2 broadly comprising a syringe 4, a catheter 6, and a guide member 8 (see FIGS. 2-4). The apparatus 2 also broadly includes side wall means 10 for defining a fluid-receiving chamber and movement means 12 for moving the guide member 8 (see FIGS. 2-4).

The syringe 4 includes a support body 14. In the preferred embodiments the support body 14 is cylindrically shaped to form a barrel portion in a manner similar to an ordinary syringe barrel; however, the barrel portion or support body 14 of the preferred embodiments is distinguishable from an ordinary syringe barrel by having a first compartment 16 and a second compartment 18 defined therein. The first compartment 16 is similar to the fluid-receiving or fluid-containing portion of an ordinary syringe. The second compartment 18, on the other hand, is an additional part of the support body 14 not commonly found on ordinary syringes.

The first and second compartments 16, 18 are defined in the preferred embodiments by the cylindrical wall defining the barrel portion. The first and second compartments 16, 18 are separated from each other by a divider element 20 having a first opening 22 therethrough. The opening 22 permits communication between the two compartments 16 and 18.

The second compartment 18 is also bounded by an end wall 24 of the support body 14. The end wall 24 has a second opening 26 defined therethrough. In the preferred embodiments shown in the drawings, the opening 26 is shown to extend through a neck portion 28 protruding from the end wall 24.

The side wall of the support body 14 defining the second compartment 18 has a third opening 30 defined therethrough. In the preferred embodiment the opening 30 is an elongated slot. The ends of the slot 30 provide means for limiting the length of travel of the guide member 8 so that the guide member 8 cannot be inadvertently pulled from its association with the syringe 4 as will be more particularly described hereinbelow. The opening 30 can include notches (not shown) or other detent means for providing discrete incremental control of the guide member 8.

The aforementioned portions of the support body 14 of the preferred embodiment are formed as an integral unit of plastic or other suitable material.

The syringe 4 also includes a plunger element 32 movably disposed in the first compartment 16 so that the extent to which the plunger 32 can be moved into the barrel portion or support body 14 is limited by the divider element 20. The plunger element 32 includes a piston head element 34 connected to a shaft 36 in a manner as is known to the art. The piston head element 34 and the guide element 8 are so associated in the preferred embodiments of the apparatus 2 that the piston head element 34 is closer to a first end 38 of the guide member 8 than to a second end 40 of the guide member 8.

The syringe 4 further includes a needle 42. The needle 42 has a passageway 44 defined therethrough for receiving fluid from a vessel into which the needle 42 can be inserted. The passageway 44 is defined by the cylindrically shaped wall forming the needle 42. In the preferred embodiment the wall of the needle 42 is constructed of steel or other suitable material.

The needle 42 also includes a first end 46 associated with the barrel portion 14 so that the passageway 44 communicates with the second opening 26 defined through the neck portion 28 and the end wall 24 of the barrel portion 14. In the embodiment shown in FIG. 2, the first end 46 is flared outwardly for compressively and frictionally engaging with the neck portion 28 of the barrel portion 14. In another preferred embodiment illustrated in FIG. 4, the end 46a extends through the opening 26 into the second compartment 18 of the barrel portion 14. In this alternative embodiment, the needle 42 is properly secured to the barrel portion 14 by suitable means known to the art, such as by constructing the neck portion 28 to apply compressive and frictional forces to the needle.

The needle 42 also includes a second end 48 spaced from the barrel portion 14. The second end 48 is beveled as shown in the figures to enhance the tissue-piercing capability of the needle 42. As also shown in the drawings, the second end 48 of the needle 42 extends beyond the end of the catheter 6 when the catheter 6 is fully mounted over the needle 42.

The catheter 6 is of a type known to the art. In particular, the catheter 6 is constructed so that it is inserted into a vessel by riding "piggyback" on a needle which is used to pierce the wall of the vessel into which the catheter 6 is to be inserted. The catheter 6 has an axial opening through which the needle 42 is slidably disposed.

The guide member 8 includes an elongated, flexible structure such as a helical steel wire or other suitable structure. As mentioned hereinabove, the guide member 8 includes a first end 38 and a second end 40. The first end 38 is disposed within the support body 14 externally of the passageway 44 and, in the preferred embodiment, within the second compartment 18. The second end 40 is made suitably blunt and/or flexible so that it cannot pierce the vessel wall, and it is disposed so that it is movable from a first locus 50 within the passageway 44 to a second locus 52 external of both the passageway 44 and the support body 14. As shown in the drawings the guide member 8 extends from its first end 38 through the opening 26 and the passageway 44 to its second end 40. As also shown in the drawings, the first end 38 is more particularly disposed within the side wall means 10 which is within the second compartment 18.

In the preferred embodiments the first locus 50 is shown adjacent the second end 48 just inside the needle 42. The second locus 52 is spaced from the second end 48 by an amount in the preferred embodiments of approximately one to one and one-half inches; however, any other suitable spacing between the first locus 50 and the second locus 52 may be used. In the preferred embodiments the spacing between the first and second loci 50, 52 is defined by the length of the slot 30.

The side wall means 10 is associated with the support body 14 to define a sterile fluid-receiving chamber having an opening through which a fluid in the passageway 44 of the needle 42 is receivable into the chamber. More particularly, in the preferred embodiments shown in the figures, the side wall means includes two openings, one of which is associated with the first opening 22 and a second of which is associated with the opening 26 to provide a channel through which a fluid can flow between the first and second openings without the fluid entering that portion of the second compartment 18 external to the side wall means 10. In the preferred embodiments shown in the drawings, the side wall means 10 includes a first flexible member 54, a second flexible member 56 and a more rigid connector member 58 for connecting the first and second flexible members 54 and 56. The member 58 is an outer cylinder which is slidable over an inner cylinder 64 protruding inwardly into the compartment 18 from the end wall 24 and forming in the preferred embodiment a part of the unitary structure defining the barrel portion 14. The flexible members 54 and 56 are responsive to compressive and tensile forces exerted thereon by the movement means 12 so that the flexible members contract and expand accordingly.

The elements 54, 56 and 58 are preferably made of a transparent material, such as transparent plastic, so that the fluid, such as blood, received in the chamber defined by the elements can be observed to inform the user of the apparatus when the second end 48 of the needle 42 has passed into a fluid-containing vessel.

Although the preferred embodiment of the side wall means 10 shown in the drawings includes flexible, bellows-like structures, any other suitable type of construction can be used so long as the structure provides a fluid channel sealed from the remainder of the second compartment 18 and permits viewing of any fluids received in the channel. For example, concentrically disposed cylinders slidingly and fluid-tightly related can be used.

Associated with the side wall means 10, the guide member 8 and the third opening 30, is the movement means 12. In the preferred embodiment the movement means 12 includes a connector means 66 for connecting the guide member 8 to the sealing wall means 10. The connector means 66 can be, for example, a suitable spider element for retaining the guide member 8 in axial alignment with the passageway 44, the connector member 58 and the inner cylinder 64.

The preferred embodiment of the movement means 12 also includes a slide arm 68 having a first end secured with, such as by being integrally formed with, the connector member 58. The slide arm 68 protrudes radially outwardly from the member 58 through the opening 30 so that a segment 70 extends outwardly from the barrel portion 14 in such a manner that the segment 70 is responsive to engagement by the thumb of the dominant hand of the user of the apparatus 2 wherein the dominant hand is the hand for holding and manipulating the syringe 4. Although the segment 70 is shown to protrude from the barrel portion 14 at a location adjacent the second compartment 18, the slide arm 68 can be so constructed that a segment 70a is located adjacent the first compartment 16 and extends to a position near a mouth 72 of the first compartment 16 as shown in FIG. 4. Suitable retaining means such as a collar or straps (not shown) can be used to retain the portion 70a adjacent the syringe body.

The movement means 12 is utilized to move the guide member 8 between the first and second loci 50, 52. More particularly, the movement means moves the guide member 8 between a fully retracted position and a fully extended position. The fully retracted position is that position wherein the first guide member end 38 is positioned at the locus depicted in FIG. 2 within the chamber defined by the side wall means 10 and the second guide member end 40 is positioned within the passageway 44 at the locus 50. The fully extended position is that position wherein the first guide member end 38 is positioned at the locus within the chamber as shown in FIG. 3 and the second guide member end 40 is positioned external to the passageway 44 and the needle 42 at the second locus 52. Through the coaction of the slide arm 68 and the limiting means defined by the ends of the opening 30, the length of travel of the guide member 8 through the passageway 44 of the needle 42 is limited to the extent that the first locus 50 is always maintained within the passageway 44 whereby the guide member 8 is prevented from being separated from the syringe 4.

The second preferred embodiment illustrated in FIG. 4 contains elements similar to those described with respect to FIGS. 1–3 as indicated by the like reference numerals used in FIG. 4. One distinction between the embodiment shown in FIG. 4 and the first embodiment is the association at the end 46a of the needle 42 with the body 14 as described hereinabove. Another distinction is the segment 70a.

With reference to all the drawings, the method of operation of the present invention will be described. This method pertains to the insertion into the lumen of a vessel of a body of a catheter mounted on a hollow needle affixed to a syringe wherein the needle has a guide member disposed therewithin. The vessel can be a vein, artery or other vessel of the body suitable for receiving the apparatus 2.

To utilize the apparatus 2, as in the case of a vein, the apparatus user first grasps the patient's arm with his or her non-dominant hand to fix the skin overlying the subcutaneous tissue and the vessel with the thumb of the non-dominant hand. This maintains the relationship between the bodily structures constant.

The user then grasps and holds the syringe 4 in his or her dominant hand in a manner known to the art. The dominant hand is moved so that the needle 42 of the apparatus 2 is inserted into the vessel until the vascular fluid, blood in this case, is received in the syringe 4 as evidenced by the fluid appearing in the chamber defined by the side wall means 10. If the fluid pressure in the vessel is too low or it is otherwise desired to assist the flow of the vascular fluid into the syringe 4, suction can be applied to the vascular fluid by moving the plunger 32 outwardly toward the mouth 72 of the syringe 4.

Once the vessel has been penetrated by the second end 48 of the needle 42, the thumb of the dominant hand engages the segment 70 (or 70a for the embodiment of FIG. 4) of the slide arm 68. The slide arm 68 is moved forward under pressure applied by the thumb of the dominant hand so that the second end 40 of the guide member 8 moves forward from the first locus 50 toward the second locus 52 within the lumen of the vessel. While the thumb of the dominant hand is moving the guide member 8 into the vessel, the dominant hand retains its hold on the syringe 4 and the nondominant hand retains its hold on the patient's body to maintain the constant relationship between the bodily structures and the placement of the syringe 4. The guide member can be advanced in or retained at discrete incremental steps if a detent means is associated with the opening 30 and the slide arm 68.

Through this operation the guide member 8 is retained within the syringe 4 until ready for use so that it is maintained sterile, and the hands are maintained positioned as they were at the time when the needle encountered the vessel.

Once the guide member 8 has been advanced out of the hollow needle 42 and into the lumen of the vessel thereby establishing a suitable mechanical link with the vessel, the catheter 6 is moved off the needle 42 and along the advanced guide member 8 into proper placement in the lumen of the vessel. Once the catheter 6 is properly positioned in the vessel, the syringe 4 and the guide member 8 are withdrawn from their association with the vessel-containing body thereby completing the proper intravascular insertion of the catheter 6.

If the end 48 of the needle 42 was not properly stopped within the lumen of the vessel prior to the step of advancing the guide member into the vessel, the guide member 8 will encounter a resistance presented by the relatively dense subcutaneous tissue or vessel wall. If this occurs, the second end 40 of the guide wire 8 can be used as a probe to find the center of the vessel and the needle 42 can be gently manipulated back and forth until the end 40 of the guide wire 8 passes freely into the lumen of the vessel.

From the foregoing it is apparent that the apparatus 2 is constructed so that the guide member 8 is maintained in a sterile environment within the syringe 4 prior to the time at which the needle 42 is inserted into the body. Once the needle 42 is inserted into the body, the guide member 8 can be advanced into the vessel without first disassembling any portion of the apparatus as is necessary with the prior art device described hereinabove.

Additionally, the present invention permits the hands of the apparatus user to be retained in their original positions even during manipulation of the guide member 8.

The present invention also is constructed and utilized so that it can be determined when a vessel containing fluid has been entered. When such vessel is encountered, the fluid will flow therefrom into the viewing area of the present invention if sufficient vascular pressure is present. In the event the pressure is too low, a suction can be provided with the present invention to extract the fluid from the vessel.

Thus, the present invention is well adapted to carry out the objects and attain the ends and advantages mentioned above as well as those inherent therein. While preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. An intravascular insertion apparatus, comprising:
   a suppport body including a syringe having a needle associated therewith, said needle having a passageway defined therethrough and said needle being slidably disposable within a catheter;
   an elongated guide member slidably disposed in said passageway, said guide member having a first end disposed within said syringe externally of said passageway and having a second end disposed for being movable from a first locus within said passageway to a second locus externally of both said passageway and syringe; and
   movement means, associated with said syringe and responsive to finger action of a hand maintaining a continuous hold on said syringe, for moving said guide member between said first and second loci independently of movement of the catheter when said needle is slidably disposed in the catheter.

2. An apparatus as defined in claim 1, wherein said syringe has a plunger element disposed closer to said first end of said guide member than to said second end of said guide member.

3. An intravascular insertion apparatus, comprising:
   a support body;
   a needle associated with said support body, said needle having a passageway defined therethrough and said needle being slidably disposable within a catheter;
   an elongated guide member slidably disposed in said passageway, said guide member having a first end disposed within said support body externally of said passageway and having a second end disposed for being movable from a first locus within said passageway to a second locus externally of both said passageway and support body;
   movement means, responsive to finger action of a hand maintaining a continuous hold on said support body, for moving said guide member between said first and second loci independently of movement of the catheter when said needle is slidably disposed in the catheter; and
   movable side wall means for defining a fluid-receiving chamber having an opening through which a fluid in said passageway of said needle is receivable into said chamber, said side wall means being associated with said support body adjacent said needle.

4. An apparatus as defined in claim 3, wherein said side wall means includes a flexible member responsive to compressive and tensile forces exerted thereon via said movement means.

5. An intravascular insertion apparatus, comprising:
   a syringe, including:
      a barrel portion having a first compartment and a second compartment defined therein, said first and second compartments being separated by a divider element having a first opening therethrough, and said barrel portion also having a wall through which are defined second and third openings communicating with said second compartment;
      a plunger movably disposed in said first compartment so that the extent to which said plunger can be moved into said barrel portion is limited by said divider element; and
      a needle having a passageway defined therethrough, having a first end associated with said barrel portion so that said passageway communicates with said second opening defined in said barrel portion, and having a second end spaced from said barrel portion;
   a sealing wall means, disposed within said second compartment, for establishing a chamber through which a fluid can flow between said first and second openings without the fluid entering that portion of said second compartment external to said sealing wall means;
   a guide member extending from a first guide member end disposed in said chamber through said second opening into said needle passageway to a second guide member end; and
   movement means, associated with said third opening, said sealing wall means and said guide member, for moving said guide member between a fully retracted position wherein said first guide member end is at a first position within said chamber and said second guide member end is positioned within said passageway of said needle and a fully extended position wherein said first guide member end is at a second position within said chamber and said second guide member end is positioned external to said passageway and said needle.

6. An apparatus as defined in claim 5, further comprising a catheter having said needle inserted therethrough so that said second end of said needle extends beyond said catheter when said needle is fully inserted through said catheter.

7. An apparatus as defined in claim 6, wherein said sealing wall means includes a flexible member which is expandable and contractable in response to said movement means.

8. An apparatus as defined in claim 6, wherein said movement means includes:
   connector means for connecting said guide member to said sealing wall means; and
   a slide arm connected to said sealing wall means and extending through said third opening of said barrel portion.

9. An apparatus as defined in claim 8, wherein said slide arm includes a segment extending outwardly of said barrel portion from said third opening, said segment being responsive to engagement by the thumb of a dominant hand of a user of said apparatus, said dominant hand being the hand of the user for holding and manipulating said syringe.

10. An apparatus as defined in claim 9, wherein said sealing wall means includes a flexible member which is expandable and contractable in response to said movement means.

11. An apparatus as defined in claim 10, further comprising a catheter having said needle inserted therethrough so that said second end of said needle extends beyond said catheter when said needle is fully inserted through said catheter.

12. A method of inserting into the lumen of a fluid-containing vessel of a body a catheter mounted on a hollow needle affixed to a syringe, the needle having a guide member disposed therewithin, comprising the steps of:
   holding the syringe in one hand;
   inserting the needle affixed to the syringe into the vessel until fluid is received in the syringe;

moving the guide member with the thumb of said one hand while retaining said one hand's hold on said syringe so that the guide member advances out of the hollow needle into the lumen of the vessel;

sliding the catheter off the needle and along the advanced guide member into placement in the lumen of the vessel; and withdrawing the syringe, needle and guide member from their association with the body.

13. An intravascular insertion apparatus, comprising:
a support body;
a needle associated with said support body, said needle having a passageway defined therethrough;
an elongated guide member slidably disposed in said passageway, said guide member having a first end disposed within said support body externally of said passegeway and having a second end disposed for being movable from a first locus within said passageway to a second locus externally of both said passageway and support body;
movement means for moving said guide member between said first and second loci; and
side wall means, associated with said support body, for defining a fluid-receiving chamber having an opening through which a fluid in said passageway of said needle is receivable into said chamber, said side wall means including a flexible member responsive to compressive and tensile forces exerted thereon via said movement means.

* * * * *